(12) United States Patent
Tokunaga

(10) Patent No.: US 7,776,806 B2
(45) Date of Patent: Aug. 17, 2010

(54) HAIR CLEANSING COMPOSITION

(75) Inventor: Shinichi Tokunaga, Sumida-ku (JP)

(73) Assignee: Kao Corporation, Tokyo (JP)

( * ) Notice: Subject to any disclaimer, the term of this patent is extended or adjusted under 35 U.S.C. 154(b) by 485 days.

(21) Appl. No.: 11/393,921

(22) Filed: Mar. 31, 2006

(65) Prior Publication Data

US 2006/0223728 A1 Oct. 5, 2006

(30) Foreign Application Priority Data

Apr. 1, 2005 (JP) ............................. 2005-106451

(51) Int. Cl.
| C11D 1/14 | (2006.01) |
| C11D 1/29 | (2006.01) |
| C11D 3/34 | (2006.01) |
| C11D 3/20 | (2006.01) |
| C11D 3/43 | (2006.01) |
| C11D 3/44 | (2006.01) |

(52) U.S. Cl. .................. 510/127; 510/137; 510/138; 510/158; 510/159; 510/477; 510/488; 510/495; 510/500; 510/505; 510/506; 424/70.24

(58) Field of Classification Search ................ 510/127, 510/128, 130, 137, 138, 158, 159, 477, 488, 510/495, 500, 505, 506; 424/70.24
See application file for complete search history.

(56) References Cited

U.S. PATENT DOCUMENTS

| 5,137,715 | A | * | 8/1992 | Hoshowski et al. ...... 424/70.17 |
| 5,403,517 | A | | 4/1995 | Horinishi et al. |
| 5,641,480 | A | | 6/1997 | Vermeer |
| 2003/0125224 | A1 | * | 7/2003 | Seitz et al. .................. 510/131 |
| 2003/0185783 | A1 | * | 10/2003 | Terazaki .................. 424/70.12 |
| 2004/0156810 | A1 | | 8/2004 | Tachizawa et al. |
| 2004/0235689 | A1 | * | 11/2004 | Sakai et al. ................. 510/119 |

FOREIGN PATENT DOCUMENTS

| JP | 5-43425 | 2/1993 |
| JP | 5-43426 | 2/1993 |
| JP | 5-286828 | 11/1993 |
| JP | 5-286830 | 11/1993 |
| JP | 6-172131 | 6/1994 |
| JP | 8-92043 | 4/1996 |
| JP | 8-198732 | 8/1996 |
| JP | 2000-327536 | 11/2000 |
| JP | 2004-182653 | 7/2004 |
| JP | 2004-203866 | 7/2004 |
| JP | 2004-315448 | 11/2004 |
| WO | WO 00/72807 | 12/2000 |
| WO | WO 03/088940 A1 | 10/2003 |
| WO | 2004/004677 A1 | 1/2004 |

OTHER PUBLICATIONS

Japanese Office Action issued on Mar. 30, 2010.

* cited by examiner

*Primary Examiner*—Gregory R Del Cotto
(74) *Attorney, Agent, or Firm*—Oblon, Spivak, McClelland, Maier & Neustadt, L.L.P.

(57) ABSTRACT

A hair cleansing composition containing the following Components (A) to (D):

(A) a sulfate surfactant represented by the following formula (1):

$$R^1-O-(C_2H_4O)_n-SO_3M \qquad (1)$$

(wherein, $R^1$ represents a $C_{10-18}$ alkyl or alkenyl, n stands for 0 or a positive integer and M represents sodium or ammonium), composed of from 30 to 45 wt. % of a sulfate exhibiting n=0, from 18 to 27 wt. % of a sulfate exhibiting n=1, from 10 to 20 wt. % of a sulfate exhibiting n=2 and the balance of sulfates exhibiting n=3 or greater, and containing the sulfates exhibiting n=0 to 2 in a total amount of 70 wt. % or greater based on the total sulfates, (B) a $C_{6-18}$ hydrophobic sulfonic acid or salt thereof, (C) a hydroxycarboxylic acid, dicarboxylic acid or aromatic carboxylic acid, (D) an organic solvent; and having a pH of 2 or greater but less than 6.

The hair cleansing composition according to the present invention is excellent in the hair feel during shampooing and effects for straightening the flyaway or waved hair tip, which has resulted from the accumulation of damages caused, for example, by hair coloring.

8 Claims, No Drawings

HAIR CLEANSING COMPOSITION

FIELD OF THE INVENTION

The present invention relates to a hair cleansing composition containing a hydrophobic sulfonic acid.

BACKGROUND OF THE INVENTION

Hair tends to be excessively dry because of daily shampooing, brushing or heat from a drier in addition to exposure to ultraviolet rays or sun shining. In recent years, it has been common to enjoy changing the appearance of hair such as changing hair color (coloring) and changing hair style (permanent waving) frequently. Repetition of them however damages the hair and increases the friction between the surfaces of individual hairs. This tends to result in the entanglement of hair, deterioration of the hair feel during shampooing or disruption of smooth combing after drying. In addition, since a curl different from the intended one appears at the hair tip because of damages accumulated therein, the hair inevitably goes in various directions. Such a symptom is known as "flyaway hair" or "jumping hair". This leads to the hair troubles of consumers such as stiffness, unmanageability and difficulty in setting.

In order to improve the hair feel during shampooing and manageability of the hair, a cationic polymer, silicone derivative, oily substance and the like are added to a hair cleansing composition. For example, there is a proposal to incorporate a cationic polymer or silicone in a hair cleansing composition for the purpose of improving the hair feel during shampooing and combing ease of the hair (JP-A-S56-72095). Another approach is addition of an organic acid to a hair cosmetic composition in order to soften the hair, thereby improving its manageability (JP-A-H06-172131). Even if these technologies are applied to the hair damaged by coloring or the like, they cannot bring about satisfactory improvements in both the hair feel during shampooing and effects for alleviating the unwanted curls of the hair tip resulting from the accumulation of damages.

Hydrophobic sulfonic acids such as naphthalenesulfonic acid and benzophenonesulfonic acid have recently been incorporated in hair treatment compositions or curly hair straightening compositions such as hair deforming compositions and are known to give body/strength to the hair (for example, JP-A-H05-43425, JP-A-H05-43426, JP-A-H05-286828, JP-A-H05-286830, JP-A-H08-198732, and JP-A-H08-92043).

SUMMARY OF THE INVENTION

In the present invention, there is provided a hair cleansing composition containing the following components (A) to (D):

(A) a sulfate surfactant represented by the following formula (1):

(wherein, $R^1$ represents a linear or branched alkyl or alkenyl group having from 10 to 18 carbon groups, n stands for 0 or a positive integer and M represents sodium or ammonium), composed of from 30 to 45 wt. % of a sulfate exhibiting n=0, from 18 to 27 wt. % of a sulfate exhibiting n=1, from 10 to 20 wt. % of a sulfate exhibiting n=2 and the balance of sulfates exhibiting n=3 or greater, and containing the sulfates exhibiting n=0 to 2 in a total amount of 70 wt. % or greater based on the total sulfates, . . . .

(B) a hydrophobic sulfonic acid having from 6 to 18 carbon atoms or salt thereof, (C) an organic acid selected from hydroxycarboxylic acids, dicarboxylic acids and aromatic carboxylic acids, (D) an organic solvent selected from the following compounds (d1) to (d5):

(d1) compounds represented by the formula (2):

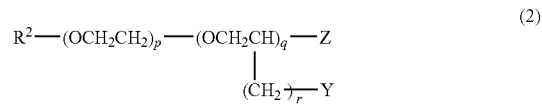

(wherein, $R^2$ represents a hydrogen atom, an alkyl group having from 1 to 6 carbon atoms or a group $R^3$-Ph-$R^4$— ($R^3$: a hydrogen atom, a methyl group or a methoxy group, $R^4$: a bond or a saturated or unsaturated divalent hydrocarbon group having from 1 to 3 carbon atoms, Ph: phenylene group), Y and Z each represents a hydrogen atom or a hydroxy group, p, q and r each stands for an integer of from 0 to 5, with the proviso that when p=q=0, Z represents a hydroxy group and $R^2$ represents neither a hydrogen atom nor a group $R^3$-Ph-), (d2) N-alkylpyrrolidones having a $C_{1-18}$ alkyl group bonded to a nitrogen atom, (d3) alkylene carbonates having from 2 to 4 carbon atoms, (d4) propylene glycols having a molecular weight of from 200 to 5000, and (d5) lactones or cyclic ketones represented by the following formula (3), (4) or (5):

(wherein, X represents a methylene group or an oxygen atom, $R^5$ and $R^6$ represent different substituents, and a and b stands for 0 or 1); and having a pH at 25° C. of 2 or greater but less than 6 when diluted to 20 times the weight with water.

DETAILED DESCRIPTION OF THE INVENTION

The present invention relates to a hair cleansing composition excellent in the hair feel during shampooing and effective for straightening the hair tip which has been flyaway or waved owing to damages accumulated by the repetition of hair coloring or the like, thereby returning it into its original state.

The present inventors have found that by using a combination of specific sulfate surfactant, hydrophobic sulfonic acid, organic acid and organic solvent, a hair cleansing composition capable of satisfying the above-described demands can be prepared.

The sulfate surfactant serving as Component (A) is represented by the following formula (1):

$$R^1—O—(C_2H_4O)_n—SO_3M \quad (1).$$

In the present invention, a hair cleansing composition capable of providing foam of good quality abundantly and giving comfortable feel to the hair can be obtained by adopting a sulfate surfactant showing a specific distribution in the number of moles of ethylene oxide and composed mainly of sulfates having a small number of moles of ethylene oxide, that is, a sulfate surfactant composed of from 30 to 45 wt. % of a sulfate exhibiting n=0, from 18 to 27 wt. % of a sulfate exhibiting n=1, from 10 to 20 wt. % of a sulfate exhibiting n=2 and the balance of sulfates exhibiting n=3 or greater, and at the same time, containing the sulfates exhibiting n=0 to 2 in a total amount of 70 wt. % or greater based on the total sulfates. The sulfate surfactant having such a distribution is preferably composed of sulfates having the same alkyl chain length and only different in the number of moles of ethylene oxide added.

With regard to the distribution of n which is the number of moles of ethylene oxide added, the sulfate surfactant is preferably composed of from 33 to 43 wt. % of a sulfate exhibiting n=0, from 20 to 25 wt. % of a sulfate exhibiting n=1, from 13 to 18 wt. % of a sulfate exhibiting n=2 and the balance of sulfates exhibiting n=3 or greater, more preferably from 35 to 41 wt. % of a sulfate exhibiting n=0, from 21 to 23 wt. % of a sulfate exhibiting n=1, from 14 to 17 wt. % of a sulfate exhibiting n=2 and the balance of sulfates exhibiting n=3 or greater from the viewpoint of giving a fine feel of foam to the damaged hair. The proportion of the sulfates exhibiting n=0 to 2 in the sulfate surfactant component is 70 wt. % or greater, preferably from 70 to 85 wt. % based on the total sulfates from the same viewpoint.

Such sulfate surfactant can be prepared by sulfating an alcohol ethoxylate, which has been obtained by adding from 0.85 to 1.35 times the mole of ethylene oxide to a higher alcohol $R^1OH$, with from 0.95 to 1.0 equivalent of $SO_3$ and then neutralizing the resulting sulfate with sodium hydroxide or ammonia. In formula (1), M preferably represents ammonium from the standpoint of imparting the damaged hair with comfortable feel of foam.

The content of the sulfate surfactant (A) is preferably from 5 to 30 wt. %, more preferably from 7 to 23 wt. %, even more preferably from 10 to 20 wt. % in the hair cleansing composition of the present invention from the viewpoints of good foaming property and abundant amount of foam during shampooing and smooth foam quality.

Examples of the hydrophobic group of the hydrophobic sulfonic acid (B) having from 6 to 18 carbon atoms include aliphatic hydrocarbon groups, alicyclic hydrocarbon groups, aromatic hydrocarbon groups and heterocyclic groups. The hydrocarbon groups containing an aromatic ring preferably have from 6 to 18 carbon atoms, while the hydrocarbon groups containing no aromatic ring preferably have from 6 to 9 carbon atoms. Such hydrophobic sulfonic acids include the following ones (b1) to (b3).

(b1) aromatic sulfonic acids having from 6 to 18 carbon atoms and containing an aromatic ring (b2) aromatic sulfonic acid having from 10 to 18 carbon atoms and containing at least two aromatic rings (b3) aliphatic sulfonic acids having an aliphatic hydrocarbon group with 6 to 9 carbon atoms.

As (b1), aromatic sulfonic acids having from 6 to 12 carbon atoms and containing an aromatic ring are more preferred and specific examples include benzenesulfonic acid, o-toluenesulfonic acid, p-toluenesulfonic acid, xylenesulfonic acid, cumenesulfonic acid, ethylbenzenesulfonic acid, 2,4,6-trimethylbenzenesulfonic acid, tetralinsulfonic acid, indanesulfonic acid, and phenolsulfonic acid. Of these, p-toluenesulfonic acid, xylenesulfonic acid and cumenesulfonic acid are more preferred.

As (b2), aromatic sulfonic acids having from 10 to 12 carbon atoms and containing at least two aromatic rings are more preferred. Specific examples include azulenesulfonic acid and naphthalenesulfonic acid, of which naphthalenesulfonic acid is more preferred.

As (b3), aliphatic sulfonic acids having an aliphatic hydrocarbon group with from 7 to 9 carbon atoms are more preferred. Examples include 1-heptanesulfonic acid, 1-octanesulfonic acid, 1-nonanesulfonic acid and 2-ethylhexylsulfonic acid, of which 2-ethylhexylsulfonic acid is more preferred.

As salts of these hydrophobic sulfonic acids, sodium salts, potassium salts and ammonium salts are preferred.

These hydrophobic sulfonic acids or salts thereof as Component (B) may be used in combination of two or more. The content of Component (B) is preferably from 0.1 to 5 wt. %, more preferably from 0.1 to 2 wt. %, still more preferably from 0.2 to 1 wt. % in the hair cleansing composition of the present invention in order to obtain both a smooth feel during shampooing and effect for alleviating the unwanted wave caused by the accumulation of damages.

The organic acid (C) is selected from hydroxycarboxylic acids, dicarboxylic acids and aromatic carboxylic acids. Examples of the hydroxycarboxylic acids include glycolic acid, lactic acid, hydroxyacrylic acid, oxybutyric acid, glyceric acid, malic acid, tartaric acid, citric acid and salicylic acid; examples of the dicarboxylic acids include malonic acid, succinic acid, glutaric acid, adipic acid, maleic acid, fumaric acid, phthalic acid, malic acid and tartaric acid; and examples of the aromatic carboxylic acids include salicylic acid and benzoic acid. Of these, α-hydroxycarboxylic acids are preferred, with lactic acid and malic acid being more preferred.

These organic acids (C) may be used in combination of two or more. The content of Component (C) is preferably from 0.05 to 10 wt. %, more preferably from 0.1 to 5 wt. %, still more preferably from 0.3 to 2 wt. % in the hair cleansing composition of the present invention.

Of the organic solvents as Component (D), examples of (d1) include ethanol, 1-propanol, 2-propanol, butanol, isobutanol, ethylene glycol, propylene glycol, 1,3-butanediol, benzyl alcohol, cinnamyl alcohol, phenethyl alcohol, p-anisyl alcohol, p-methylbenzyl alcohol, phenoxyethanol, 2-benzyloxyethanol, methyl carbitol, ethyl carbitol, propyl carbitol, butyl carbitol, triethylene glycol monomethyl ether, triethylene glycol monobutyl ether and glycerin.

Examples of (d2) include N-methylpyrrolidone, N-octylpyrrolidone and N-laurylpyrrolidone.

Examples of (d3) include ethylene carbonate and propylene carbonate.

The polypropylene glycol as (d4) preferably has a molecular weight of from 200 to 1000.

In the lactone or the cyclic ketone (d5) represented by the formula (3), (4) or (5), $R^5$ and $R^6$ are each preferably a linear, branched or cyclic alkyl group, hydroxy group, sulfonic acid group, phosphoric acid group, carboxy group, phenyl group, sulfoalkyl group, alkyl phosphate group or carboxyalkyl group. More preferred is a linear or branched alkyl group having from 1 to 6 carbon atoms such as methyl, ethyl, propyl, isopropyl or butyl substituted at the γ-position in the case of γ-lactone and at the δ-position (that is, methylene adjacent to the hetero oxygen atom) in the case of δ-lactone. When enhancement of water solubility of Compounds (3) to (5) is intended, $R^5$ or $R^6$ is preferably an acidic group such as sulfonic acid group, phosphoric acid group or carboxy group or an alkyl group substituted therewith. As (d5), examples of the lactone include γ-butyrolactone, γ-caprolactone, γ-valerolactone, δ-valerolactone, δ-caprolactone, and δ-heptanolactone. From the viewpoint of stability of lactone, γ-lactone, preferably, γ-butyrolactone and γ-caprolactone, are preferred. Examples of the cyclic ketone (d5) include cyclopentanone, cyclohexanone, cycloheptanone and 4-methylcycloheptanone.

As Component (D), two or more of these organic solvents may be used in combination. The content of Component (D) is preferably from 0.01 to 50 wt. %, more preferably from 0.1 to 35 wt. %, still more preferably from 0.5 to 10 wt. % in the hair cleansing composition of the present invention in order to satisfy both a smooth feel during shampooing and effects for alleviating the unwanted curls of hair tip.

The hair cleansing composition of the present invention may further contain a surfactant selected from anionic surfactants other than the sulfate surfactants (A), nonionic surfactants, amphoteric surfactants, and cationic surfactants.

Examples of the anionic surfactants other than the sulfate surfactants (A) include sulfonate surfactants and carboxylate surfactants. Specific examples include alkyl sulfosuccinates, polyoxyalkylene alkyl sulfosuccinates, higher fatty acid salts, and alkyl ether carboxylic acids and salts thereof.

Two or more of these anionic surfactants other than the sulfate surfactants (A) may be used in combination. Its (their) content in the hair cleansing composition of the present invention is preferably from 0 to 10 wt. %, more preferably from 1 to 8 wt. %, still more preferably from 2 to 6 wt. % from the standpoints of liquid property upon use and detergency.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides.

Two or more of these nonionic surfactants may be used in combination. Its (their) content in the hair cleansing composition of the present invention is preferably from 0.1 to 15 wt. %, more preferably from 0.5 to 8 wt. %, still more preferably from 1 to 6 wt. %, because a good foam increasing effect can be attained at such a content.

As the amphoteric surfactant, betaine surfactants can be used. Of these, alkyldimethylaminoacetic acid betaines and fatty acid amidopropylbetaines and alkylhydroxysulfobetaines are preferred, with fatty acid amidopropylbetaines being more preferred. As the fatty acid amidopropylbetaines, those having an acyl group with from 8 to 18 carbon atoms are preferred, with those having an acyl group with from 10 to 16 atoms being more preferred. More specifically, lauramidopropyl betaine, palmamidopropyl betaine and cocamidopropyl betaine are preferred.

Two or more of these amphoteric surfactants may be used in combination. Its (their) content in the hair cleansing composition of the present invention is preferably from 0.1 to 15 wt. %, more preferably from 0.5 to 8 wt. %, still more preferably from 1 to 6 wt. %, because at such a content, good foam increasing effect can be attained.

Examples of the cationic surfactant include alkyltrimethylammonium salts, alkoxytrimethylammonium salts, dialkyldimethylammonium salts, alkyldimethylamines and salts thereof, alkoxydimethylamines and salts thereof, and alkylamidodimethylamines and salts thereof.

(i) Alkyltrimethylammonium Salts
Usable are, for example, those represented by the following formula:

$$R^{11}-N^+(CH_3)_3X^-$$

(wherein, $R^{11}$ represents an alkyl group having from 12 to 22 carbon atoms and $X^-$ represents a halide ion (preferably, a chloride ion or bromide ion)).

(ii) Alkoxytrimethylammonium Salts
Usable are, for example, those represented by the following formula:

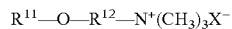

$$R^{11}-O-R^{12}-N^+(CH_3)_3X^-$$

(wherein, $R^{12}$ represents an ethylene or propylene group and $R^{11}$ and $X^-$ have the same meanings as described above).

(iii) Dialkyldimethylammonium Salts
Usable are, for example, those represented by the following formula:

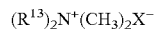

$$(R^{13})_2N^+(CH_3)_2X^-$$

(wherein, $R^{13}$ represents an alkyl having from 12 to 22 carbon atoms or benzyl group and $X^-$ has the same meaning as described above).

(iv) Alkyldimethylamines (and Salts Thereof)
Usable are, for example, those represented by the following formula:

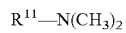

$$R^{11}-N(CH_3)_2$$

(wherein, $R^{11}$ has the same meaning as described above) and salts thereof.

(v) Alkoxydimethylamines (and Salts Thereof)
Usable are, for example, those represented by the following formula:

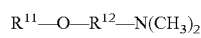

$$R^{11}-O-R^{12}-N(CH_3)_2$$

(wherein, $R^{11}$ and $R^{12}$ has the same meanings as described above) and salts thereof.

(vi) Alkylamidodimethylamines (and Salts Thereof)
Usable are, for example, those represented by the following formula:

$$R^{14}-C(=O)NH-R^{12}-N(CH_3)_2$$

(wherein, $R^{14}$ represents an alkyl group having from 11 to 21 carbon atoms and $R^{12}$ has the same meaning as described above) and salts thereof.

Examples of the cationic surfactants other than those described above in (i) to (vi) include lanolin fatty acid aminopropylethyldimethylammonium ethyl sulfate (ethyl sulfate salt of alkanoyl aminopropyldimethylethylammonium, the alkanoyl group is derived from lanolin), lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$-$C_{20}$) aminopropyldimethylammonium ethyl sulfate, isoalkanoic acid ($C_{18}$-$C_{22}$) aminopropylethyldimethylammonium ethyl sulfate, isostearic acid aminopropylethyldimethylammonium ethyl sulfate, isononanoic acid aminopropylethyldimethylammonium ethyl sulfate, and alkyltrimethylammonium saccharins.

The the hair after drying can be improved by the addition of the cationic surfactant. Two or more of these cationic surfactants may be used in combination. From the standpoint of the smoothness of the hair from shampooing to rinsing, the content of the cationic surfactant(s) in the hair cleansing composition of the present invention is preferably from 0.01 to 10 wt. %, more preferably from 0.05 to 6 wt. %, still more preferably . . . from 0.3 to 3 wt. %, still more preferably from 0.5 to 2 wt. %.

The hair cleansing composition of the present invention may further contain a cationic polymer from the viewpoints of reduction in the friction between individual hairs and improvement in the texture and a smooth feel of foam and smoothness of the hair after drying. Examples of the cationic polymer include cationic cellulose derivatives, cationic starches, cationic guar gum derivatives, homopolymers of diallyl quaternary ammonium salts, diallyl quaternary ammonium salt/acrylamide copolymers, quaternized polyvinylpyrrolidone derivatives, polyglycol polyamine condensates, vinylimidazolium trichloride/vinylpyrrolidone copolymer, hydroxyethyl cellulose/dimethyldiallylammonium chloride copolymer, vinylpyrrolidone/quaternized dimethylaminoethyl methacrylate copolymer, polyvinylpyrrolidone/alkylaminoacrylate copolymers, polyvinylpyrrolidone/alkylaminoacrylate/vinyl caprolactam copolymers, vinylpyrrolidone/methacrylamidopropyl trimethylammonium chloride copolymer, alkylacrylamide/acrylate/alkylaminoalkylacrylamide/polyethy lene glycol methacrylate copolymers, adipic acid/dimethylaminohydroxypropyl ethylene triamine copolymer ("Cartaretine", trade mark; product of Sandoz/USA), and cationic polymers described in JP-A-S53-139734 and JP-A-S60-36407. Of these, cationic cellulose derivatives, cationic guar gum derivatives and diallyl quaternary ammonium salt/acrylamide copolymers are preferred.

Two or more of these cationic polymers may be used in combination. The content of the cationic polymers in the hair cleansing composition of the present invention is preferably from 0.02 to 5 wt. %, more preferably from 0.05 to 1 wt. %, still more preferably from 0.1 to 0.7 wt. % in order to improve the foam quality during cleansing and provide manageability and a smooth feel of the hair after drying.

To the hair cleansing composition of the present invention, a silicone can be added further for improving the texture and a smooth feel of foam, reducing the friction between individual hairs and smoothness of the hair after drying. For example, silicones described below can be employed.

(1) Dimethylpolysiloxanes

Examples of them include those represented by the following formula:

$(CH_3)_3SiO—[(CH_3)_2SiO]_d—Si(CH_3)_3$ (wherein, d stands for the number of from 3 to 20000).

(2) Amino-Modified Silicones

Various amino-modified silicones can be used. Those having an average molecular weight of from about 3000 to 100000 and listed under the name of "Amodimethicone" in the third edition of CTFA Dictionary (Cosmetic Ingredient Dictionary/USA) are preferred. These amino-modified silicones are preferably employed as an aqueous emulsion. Commercially available products of them include "SM 8704C" (product of Dow Corning Toray Silicone), "DC 929" (product of Dow Corning Corporation), and "KT 1989" (product of GE Toshiba).

In addition, compounds represented by the below-described formula can be used as another amino-modified silicone. Commercially available products of them include "8500 Conditioning Agent" (CAS No. 237753-63-8) of Dow Corning.

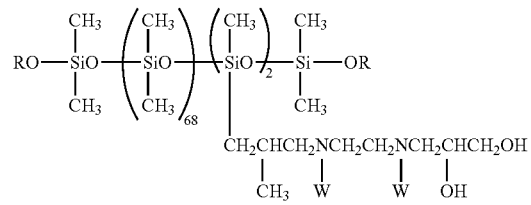

R: $C_{13}H_{27}$ to $C_{15}H_{31}$
W: a group —$CH_2CH(OH)CH_2OH$ accounts for 75%, while a hydrogen atom accounts for 25%.

(3) Other Silicones

Examples of the silicone other than those described above include polyether modified silicones, methylphenylpolysiloxane, fatty acid modified silicones, alcohol modified silicones, alkoxy modified silicones, epoxy modified silicones, fluorine modified silicones, cyclic silicones and alkyl modified silicones.

Two or more of these silicones may be used in combination. The content of the silicones in the hair cleansing composition of the present invention is preferably from 0.01 to 10 wt. %, more preferably from 0.05 to 6 wt. %, still more preferably from 0.3 to 3 wt. % from the viewpoints of the smoothness of the hair from shampooing to rinsing.

The hair cleansing composition of the present invention can further contain an oily substance as another conditioning agent. Examples of the oily substance include hydrocarbons such as squalene, squalane, liquid paraffin, liquid isoparaffin and cycloparaffin; glycerides such as castor oil, cacao oil, mink oil, avocado oil and olive oil; waxes such as beeswax, spermaceti, lanolin and carnauba wax; polyhydric alcohols such as glycerin; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut fatty acid, isostearic acid and isopalmitic acid; and higher alcohols such as myristyl alcohol, cetyl alcohol, stearyl alcohol, behenyl alcohol, 2-octyldodecanol and cetostearyl alcohol. In addition, glyceryl ethers, for example, monoalkyl glyceryl ethers or monoalkenyl glyceryl ethers having an alkyl or alkenyl group with from 4 to 12 carbon atoms (preferably a linear or branched group having from 4 to 10 carbon atoms, more preferably that having from 8 to 10 carbon atoms, even more preferably an alkyl group such as n-butyl, isobutyl, n-pentyl, 2-methylbutyl, isopentyl, n-hexyl, isohexyl, n-heptyl, n-octyl, 2-ethylhexyl, n-decyl or isodecyl group) and polyoxypropylene butyl ether are suitably employed. Of these, higher alcohols, preferably myristyl alcohol, cetyl alcohol and stearyl alcohol are preferred. Glyceryl ethers, preferably 2-ethylhexyl glyceryl ether and isodecyl glyceryl ether are effective for improving foaming power. Two or more of these oily substances can be used in combination. Content of it (them) in the hair cleansing composition of the present invention is preferably from 0.2 to 2 wt. %, more preferably from 0.3 to 1.8 wt. %, still more preferably from 0.5 to 1.5 wt. %.

The hair cleansing composition of the present invention can further contain an ethylene glycol monofatty acid ester or ethylene glycol difatty acid ester in order to improve the texture and stability of the composition. Examples of the ethylene glycol monofatty acid ester include ethylene glycol monostearate and ethylene glycol monobehenate, while those of the ethylene glycol difatty acid ester include ethylene glycol distearate and ethylene glycol dibehenate. Two or more of these esters may be used in combination and the content of it (them) in the hair cleansing composition of the present invention is preferably from 0.5 to 8 wt. %, more preferably from 0.7 to 5 wt. %, still more preferably from 1 to 3 wt. %. In view of improving stability of the cleansing composition, the weight ratio of a pearling agent containing the ethylene glycol fatty acid ester to the sulfate surfactant (pearling agent/sulfate surfactant) in the hair cleansing composition of the present invention is preferably from 1/10 to 2/5, more preferably from 1/7 to 3/10, still more preferably from 1/6 to 1/4.

The hair cleansing composition of the present invention may further contain a viscosity regulator. Examples of the viscosity regulator include hydroxyethyl cellulose, methyl cellulose, polyethylene glycol, clay minerals, and salts (sodium chloride, ammonium chloride, sodium citrate and the like). Of these, salts, for example, sodium chloride and sodium citrate are preferred. As the viscosity regulator, two or more of them may be used in combination. The content of it (or them) in the hair cleansing composition of the present invention is preferably from 0.01 to 5 wt. %, more preferably from 0.05 to 3 wt. %, more preferably from 0.1 to 1.5 wt. % from the standpoints of the amount and quality of the foam.

The hair cleansing composition of the present invention may contain, in addition to the above-described components, components used for ordinary hair cleansing compositions according to the using purpose of it. Examples of such components include anti-dandruffs; vitamin preparations; bactericides; anti-inflammatory agents; antiseptics; chelating agents; humectants such as panthenol; colorants such as dyes and pigments; extracts such as extract of Eucalyptus in a polar solvent, protein available from a pearl or a shell having a pear layer or hydrolysate of the protein, protein available from silk or hydrolysate of the protein, protein-containing extract available from seeds of legume plants, *Panax ginseng* extract, rice bran extract, fucoid extract, camellia extract, aloe extract, Alpinia Leaf extract and *chlorella* extract; pearl powder such as titanium oxide; ceramide and pseudo ceramide; perfumes; coloring matters; ultraviolet absorbers; antioxidants; and other components described in ENCYCLOPEDIA OF SHAMPOO INGREDIENTS (MICELLE PRESS).

When the hair cleansing composition of the present invention is applied to the hair, it preferably has a pH (when diluted to 20 times the weight with water, 25° C.) of 2 or greater but less than 6, more preferably from 3 to 5, still more preferably from 3.5 to 4.5 from the viewpoint of alleviating the unwanted wave of the hair tip. Examples of the pH regulator include, in addition to the organic acids used as Component (C), inorganic acids and bases such as sodium hydroxide, potassium hydroxide and ammonium chloride.

The hair cleansing composition of the present invention can be provided in the form selected as needed from liquid, gel or the like. It is preferably in the liquid form using, as a solvent, water or a lower alcohol, more preferably, water.

EXAMPLES

Preparation Example 1

Ammonium Lauryl Ether Sulfate with an Average of 1.0 mole of EO

In a pressure-resistant closed reactor were charged 2000 g of "Kalcol 2470" (trade name; product of Kao Corp., dodecyl alcohol: tetradecyl alcohol=about 3:1) and 1.45 g of potassium hydroxide, followed by dehydration at 110° C. and 10 mmHg for 30 minutes. The temperature in the system was then elevated to 165° C. After temperature elevation, 456 g of ethylene oxide was pressed in the reactor and addition reaction was performed for 30 minutes without changing the temperature. The reaction mixture was then cooled to 80° C. and neutralized with 1.3 g of acetic acid, whereby an ethylene oxide adduct of the raw material alcohol was obtained.

A sulfating reaction was conducted using 1793 g of the mixture obtained by the above-described reaction and 607 g of a sulfuric acid gas at 40° C. The reaction mixture was then neutralized with 150 g of 28 wt. % aqueous ammonia and 600 g of deionized water. The concentration and pH were regulated further by using 28 wt. % aqueous ammonia and deionized water, whereby 10000 g of a 25 wt. % aqueous solution of Sulfate 1 as listed in Table 1 was obtained.

In accordance with the Japanese Standards of Cosmetic Ingredients, the sulfate, anion and EO chain of the sulfate thus obtained were confirmed.

Preparation Example 2

Ammonium Lauryl Ether Sulfate with an Average of 1.3 Moles of EO

In a similar manner to Preparation Example 1 except that a reaction ratio of the raw materials was changed, a 25 wt. % aqueous solution of Sulfate 2 as listed in Table 1 was obtained.

In accordance with the Japanese Standards of Cosmetic Ingredients, the sulfate, anion and EO chain of the sulfate thus obtained were confirmed.

Preparation Example 3

Sodium Lauryl Ether Sulfate with an Average of 1.0 Mole of EO

A sulfating reaction was performed at 40° C. by using 1793 g of the ethylene oxide adduct of the raw material alcohol obtained in Preparation Example 1 and 607 g of a sulfuric acid gas. The reaction mixture was then neutralized with 132 g of a 23 wt. % aqueous solution of sodium hydroxide and 556 g of deionized water. By using a 23 wt. % aqueous solution of sodium hydroxide, 75 wt. % of phosphoric acid and deionized water, the concentration and pH were regulated further, whereby 10000 g of a 25 wt. % aqueous solution of Sulfate 3 as listed in Table 1 was obtained.

In accordance with the Japanese Standards of Cosmetic Ingredients, the sodium salt, sulfate, anion and EO chain of the sulfate thus obtained were confirmed.

TABLE 1

| | n (wt. %) in the formula (1) | | | | |
|---|---|---|---|---|---|
| | 0 | 1 | 2 | 3 | 4≦ |
| Sulfate 1: Component (A) (ammonium lauryl ether sulfate with an average of 1.0 mole of EO obtained in Preparation Example 1) | 40.64 | 22.29 | 14.80 | 8.68 | 13.59 |
| Sulfate 2: Component (A) (ammonium lauryl ether sulfate with an average of 1.3 moles of EO obtained in Preparation Example 2) | 34.29 | 21.41 | 16.59 | 10.09 | 17.62 |
| Sulfate 3: Component (A) (sodium lauryl ether sulfate with an average of 1.0 mole of EO obtained in Preparation Example 3) | 40.64 | 22.29 | 14.80 | 8.68 | 13.59 |
| Comparative sulfate 1 (sodium lauryl ether sulfate with an average of 2.0 moles of EO, "Emal 227", product of Kao Corp.) | 19.97 | 15.99 | 16.03 | 13.20 | 34.82 |
| Comparative sulfate 2 (mixture of sodium lauryl ether sulfate with an average of 2.0 moles of EO and sodium lauryl sulfate) | 46.43 | 10.70 | 10.73 | 8.83 | 23.31 |

Examples 1 to 14 and Comparative Examples 1 to 5

Hair cleansing compositions shown in Tables 2 and 3 were prepared using the sulfate surfactants (lauryl ether sulfates) shown in Table 1 and they were evaluated for smooth feel during shampooing and rinsing and the removal 10 degree of an unwanted curl of the hair (hair tip) after drying. The pH is a value at 25° C. when the composition is diluted to 20 times the weight with water.

(Smooth Feel During Shampooing and Rinsing)

A hair bundle of 20 cm long, 5.5 cm wide and 10.0 g in weight was formed using damaged hair obtained in advance by repeating bleaching 8 times and shampooing and drying 720 times. It was rinsed lightly with warm water of 40° C. and then excess water was wiped off. Foam was made sufficiently for about 30 seconds with 0.5 g of the hair cleansing composition. The smooth feel of the hair bundle with foam was organoleptically evaluated. Then, the smooth feel of the hair bundle was organoleptically evaluated while rinsing it with warm water of 40° C. Evaluation was made by a panel of 5 experts and a total score of them was indicated.

Evaluation Criteria:
  4: provides a good smooth feel
  3: provides a smooth feel
  2: provides a slightly smooth feel
  1: provides no smooth feel (Removal Degree of Unwanted Curl from Hair Tip)

A hair bundle of 20 cm long, 1.5 cm wide and 1.0 g in weight was formed using damaged hair obtained in advance by repeating bleaching 8 times and shampooing and drying 720 times. It was rinsed lightly with warm water of 40° C. and then extra water was wiped off. Foam was made for about 30 seconds with 0.1 g of the hair cleansing composition. After the hair bundle with foam was rinsed with running water (2 L/min) of 40° C. for 30 seconds, the hair bundle was towel-dried sufficiently and blow-dried while combing it. This operation was repeated 30 times. The resulting hair bundle was then visually evaluated for the removal degree of an unwanted wave from the hair tip. Evaluation was made by a panel of 5 experts and a total score of them was indicated.

Evaluation Criteria:
  4: An unwanted curl is removed completely.
  3: An unwanted curl is removed.
  2: An unwanted curl is slightly removed.
  1: An unwanted curl is not removed.

TABLE 2

| | (wt. %) | Examples | | | | | | | | | | |
|---|---|---|---|---|---|---|---|---|---|---|---|---|
| | | 1 | 2 | 3 | 4 | 5 | 6 | 7 | 8 | 9 | 10 | 11 |
| (A) | Sulfate 1 | 48 | | | 48 | | 48 | | | | 48 | 48 |
| | Sulfate 2 | | 48 | | | 48 | | 48 | | | | |
| | Sulfate 3 | | | 48 | | | 48 | | | 48 | | |
| (A)' | Comparative Sulfate 1 | | | | | | | | | | | |
| | Comparative Sulfate 2 | | | | | | | | | | | |
| (B) | p-Toluenesulfonic acid | 0.5 | 0.5 | 0.5 | | | | | | | 0.4 | 0.4 |
| | Sodium naphthalenesulfonate | | | | 0.5 | 0.5 | 0.5 | | | | | |
| | Sodium 2-ethylhexylsulfonate | | | | | | | 0.5 | 0.5 | 0.5 | 0.3 | 0.3 |
| (C) | Malic acid | 0.5 | 0.5 | 0.5 | 0.5 | 0.5 | 0.5 | 0.5 | 0.5 | 0.5 | 0.5 | |
| | Glycolic acid | | | | | | | | | | 0.1 | 0.5 |
| | Lactic acid | | | | | | | | | | 0.1 | 0.2 |
| (D) | Ethanol | 0.5 | 0.5 | 0.5 | 0.5 | 0.5 | 0.5 | 0.5 | 0.5 | 0.5 | 0.5 | 0.5 |
| | Benzyl alcohol | 0.5 | 0.5 | 0.5 | 0.5 | 0.5 | 0.5 | 0.5 | 0.5 | 0.5 | 0.5 | 0.5 |
| | Polypropylene glycol (Mw = 400) | 0.3 | 0.5 | 0.2 | 0.3 | 0.3 | 0.3 | 0.3 | 0.3 | 0.3 | 0.3 | 0.3 |
| Others | Amidopropylbetaine | 2 | 2 | 2 | 2 | 2 | 2 | 2 | 2 | 2 | 2 | 2 |
| | Cocoyl monoethanolamide | 1 | 1 | 1 | 1 | 1 | 1 | 1 | 1 | 1 | 1 | 1 |
| | Polyoxyethylene (14) lauryl ether | 0.8 | 0.8 | 0.8 | 0.8 | 0.8 | 0.8 | 0.8 | 0.8 | 0.8 | 0.8 | 0.8 |
| | Cationic hydroxyethyl cellulose | 0.5 | 0.5 | 0.5 | 0.5 | 0.5 | 0.5 | 0.5 | 0.5 | 0.5 | 0.5 | 0.5 |
| | Diallyl quaternary ammonium salt/acrylamide copolymer ("Merquat 550", product of Nalco) | 0.2 | 0.2 | 0.2 | 0.2 | 0.2 | 0.2 | 0.2 | 0.2 | 0.2 | 0.2 | 0.2 |
| | Highly polymerized methylpolysiloxane emulsion ("Silicone CF2450", product of Dow Corning Toray) | 2 | 2 | 2 | 2 | 2 | 2 | 2 | 2 | 2 | 2 | 2 |
| | Amino-modified silicone ("KT1989", product of Ge Toshiba Silicones)[*1] | 0.3 | 0.3 | 0.3 | 0.3 | 0.3 | 0.3 | 0.3 | 0.3 | 0.3 | 0.3 | 0.3 |
| | Amino-modified silicone ("8500 Conditioning Agent", product of Dow Corning)[*2] | | | | | | | | | | | |

TABLE 2-continued

| (wt. %) | | Examples 1 | 2 | 3 | 4 | 5 | 6 | 7 | 8 | 9 | 10 | 11 |
|---|---|---|---|---|---|---|---|---|---|---|---|---|
| | Myristyl alcohol | 0.5 | 0.5 | 0.5 | 0.5 | 0.5 | 0.5 | 0.5 | 0.5 | 0.5 | 0.5 | 0.5 |
| | Ethylene glycol distearate | 2 | 2 | 2 | 2 | 2 | 2 | 2 | 2 | 2 | 2 | 2 |
| | Isodecyl glyceryl ether | | | | | | | | | | | |
| | Potassium hydroxide*3 | q.s. | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance | Balance |
| | Total | 100 | 100 | 100 | 100 | 100 | 100 | 100 | 100 | 100 | 100 | 100 |
| | pH | 3.7 | 3.7 | 3.7 | 3.7 | 3.7 | 3.7 | 3.7 | 3.7 | 3.7 | 4.3 | 4.3 |
| Evaluation | Smoothness of foam | 20 | 20 | 20 | 20 | 20 | 20 | 20 | 20 | 20 | 20 | 20 |
| | Smoothness of hair during rinsing | 19 | 19 | 19 | 15 | 15 | 15 | 19 | 19 | 19 | 19 | 19 |
| | Removal degree of unwanted curl from hair tip | 19 | 19 | 19 | 20 | 20 | 20 | 19 | 19 | 19 | 19 | 19 |

*1
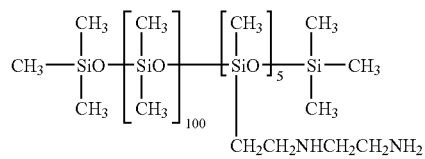

*2
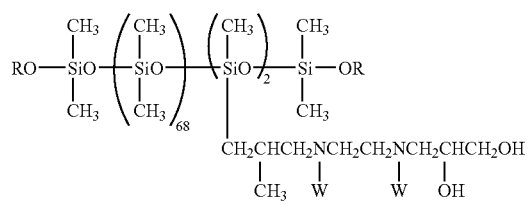

R: a hydrocarbon group of from $C_{13}H_{27}$ to $C_{15}H_{31}$
W: a group —$CH_2CH(OH)CH_2OH$ accounts for 75% and a hydrogen atom accounts for 25%.
*3 Amount to adjust pH

TABLE 3

| | (wt. %) | Examples | | | | | Comparative Examples | | | | |
|---|---|---|---|---|---|---|---|---|---|---|---|
| | | 12 | 13 | 14 | 15 | 16 | 1 | 2 | 3 | 4 | 5 |
| (A) | Sulfate 1 | 48 | 48 | 48 | 48 | 48 | 48 | 48 | 48 | | |
| | Sulfate 2 | | | | | | | | | | |
| | Sulfate 3 | | | | | | | | | | |
| (A)' | Comparative Sulfate 1 | | | | | | | | | 44.4 | |
| | Comparative Sulfate 2 | | | | | | | | | | 44.4 |
| (B) | p-Toluenesulfonic acid | 0.5 | 0.5 | 0.5 | 0.5 | 0.5 | | 0.5 | 0.5 | 0.5 | 0.5 |
| | Sodium naphthalenesulfonate | | | | | | | | | | |
| | Sodium 2-ethylhexylsulfonate | | | | | | | | | | |
| (C) | Malic acid | 0.5 | 0.5 | 0.5 | 0.5 | | 0.5 | | 0.5 | 0.5 | 0.5 |
| | Glycolic acid | | | | | | | | | | |
| | Lactic acid | | | | | 0.7 | | | | | |
| (D) | Ethanol | 0.8 | | | 0.4 | 0.5 | 0.5 | 0.5 | | 0.5 | 0.5 |
| | Benzyl alcohol | | 0.8 | | 0.6 | 0.4 | 0.5 | 0.5 | | 0.5 | 0.5 |
| | Polypropylene glycol (Mw = 400) | | | 0.8 | 0.2 | 0.4 | 0.3 | 0.3 | | 0.3 | 0.3 |
| Others | Amidopropylbetaine | 2 | 2 | 2 | 3 | 2 | 2 | 2 | 2 | 2 | 2 |
| | Cocoyl monoethanolamide | 1 | 1 | 1 | 1 | 1 | 1 | 1 | 1 | 1 | 1 |
| | Polyoxyethylene (14) lauryl ether | 0.8 | 0.8 | 0.8 | 1 | | 0.8 | 0.8 | 0.8 | 0.8 | 0.8 |
| | Cationic hydroxyethyl cellulose | 0.5 | 0.5 | 0.5 | 0.4 | 0.4 | 0.5 | 0.5 | 0.5 | 0.5 | 0.5 |
| | Diallyl quaternary ammonium salt/acrylamide copolymer ("Merquat 550", product of Nalco) | 0.2 | 0.2 | 0.2 | 0.1 | 0.3 | 0.2 | 0.2 | 0.2 | 0.2 | 0.2 |
| | Highly polymerized methylpolysiloxane emulsion ("Silicone CF2450", product of Dow Corning Toray) | 2 | 2 | 2 | 2 | 2 | 2 | 2 | 2 | 2 | 2 |
| | Amino-modified silicone ("KT1989", product of GE Toshiba Silicones)*1 | 0.3 | 0.3 | 0.3 | | | 0.3 | 0.3 | 0.3 | 0.3 | 0.3 |
| | Amino-modified silicone ("8500 Conditioning Agent", product of Dow Corning)*2 | | | | 0.4 | 0.2 | | | | | |
| | Myristyl alcohol | 0.5 | 0.5 | 0.5 | 0.5 | 0.5 | 0.5 | 0.5 | 0.5 | 0.5 | 0.5 |
| | Ethylene glycol distearate | 2 | 2 | 2 | 2 | 2 | 2 | 2 | 2 | 2 | 2 |
| | Isodecyl glyceryl ether | | | | | 1 | | | | | |
| | Potassium hydroxide*3 | q.s. | q.s. | q.s. | q.s. | q.s. | q.s. | q.s. | q.s. | q.s. | q.s. |

TABLE 3-continued

|  | (wt. %) | Examples 12 | 13 | 14 | 15 | 16 | Comparative Examples 1 | 2 | 3 | 4 | 5 |
|---|---|---|---|---|---|---|---|---|---|---|---|
|  | Purified water | Balance | Balance | Balance | Balance | Balance | Balance | Balance | Balance | Balance | Balance |
|  | Total | 100 | 100 | 100 | 100 | 100 | 100 | 100 | 100 | 100 | 100 |
|  | pH | 3.7 | 3.7 | 3.7 | 3.7 | 3.7 | 3.7 | 6.0 | 3.7 | 3.7 | 3.7 |
| Evaluation | Smoothness of foam | 20 | 20 | 20 | 20 | 20 | 20 | 20 | 20 | 14 | 15 |
|  | Smoothness of hair during rinsing | 19 | 19 | 19 | 20 | 19 | 19 | 19 | 19 | 12 | 11 |
|  | Removal degree of unwanted curl from hair tip | 19 | 19 | 19 | 19 | 19 | 9 | 6 | 12 | 19 | 19 |

*1

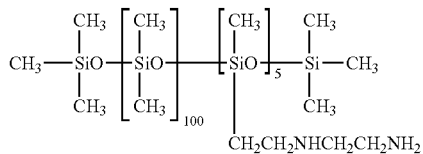

$CH_2CH_2NHCH_2CH_2NH_2$

*2

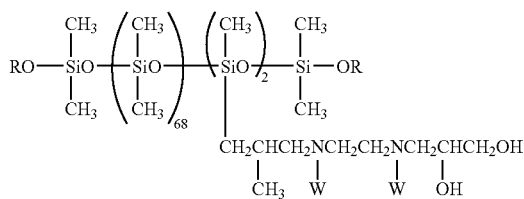

$CH_2CHCH_2NCH_2CH_2NCH_2CHCH_2OH$
$\quad\ \ |\qquad\ \ |\qquad\quad |\qquad\quad\ |$
$\ \ CH_3\ \ \ W\qquad\ \ W\qquad\ OH$ R: a hydrocarbon group of from $C_{13}H_{27}$ to $C_{15}H_{31}$
W: a group —$CH_2CH(OH)CH_2OH$ accounts for 75% and a hydrogen atom accounts for 25%.
*3 Amount to adjust pH

Example 17

Pearlescent Shampoo

| | (wt. %) |
|---|---|
| Sulfate 3 (sodium lauryl ether sulfate with an average of 1.0 mole of EO) | 48.0 |
| Sodium xylenesulfonate | 0.5 |
| Sodium Cocoanphoacetate | 0.5 |
| Cocoyl monoethanolamide | 0.3 |
| Polyoxyethylene (14) lauryl ether | 1.0 |
| Highly polymerized methylpolysiloxane emulsion ("Silicone CF2450", product of Dow Corning Toray) | 4.0 |
| Benzyl alcohol | 0.5 |
| Ethylene glycol distearate | 2.0 |
| Cationic hydroxyethyl cellulose ("Polymer JR-400", product of Amerchol) | 0.4 |
| Amino-modified silicone derivative ("8500 CONDITIONING AGENT", product of Dow Corning) | 1.0 |
| Panthenol | 0.05 |
| Silk extract | 0.05 |
| Sodium chloride | 1.0 |
| Lactic acid | Amount to adjust pH to 5.0 |
| Deionized water | Balance |

Example 18

Conditioning Shampoo

| | (wt. %) |
|---|---|
| Sulfate salt 1 (ammonium lauryl ether sulfate with an average of 1.0 mole of EO) | 52.0 |
| p-Toluenesulfonic acid | 0.5 |
| Isodecyl glyceryl ether | 0.7 |
| Lauryl amidopropylbetaine | 2.0 |
| Cocoyl monoethanolamide | 0.5 |
| Myristyl alcohol | 1.5 |
| Polyoxyethylene (16) lauryl ether | 1.0 |
| Ethylene glycol distearate | 2.0 |
| Cationic hydroxyethyl cellulose ("Poiz C-80M", trade name; product of Kao Corporation) | 0.5 |
| Diallyl quaternary ammonium salt/acrylamide copolymer ("Merquat 550", trade name; product of ONDEO NALCO) | 0.2 |
| Amino-modified silicone derivative ("8500 CONDITIONING AGENT", product of Dow Corning) | 0.4 |
| Highly polymerized methylpolysiloxane emulsion ("Silicone CF2450"; product of Dow Corning Toray) | 2.0 |
| Benzyl alcohol | 0.4 |
| Polypropylene glycol (Mw = 400) | 0.2 |
| Hydrolyzed conchiolin solution (dry content: 3 wt. %) | 0.05 |
| Panax ginseng extract (dry content: 3 wt. %) | 0.05 |
| Soybean extract (dry content: 0.4 wt. %) | 0.05 |
| Eucalyptus extract (dry content: 0.2 wt. %) | 0.05 |
| Camellia oil | 0.05 |
| Rice bran oil | 0.05 |
| Malic acid | 0.5 |
| Sodium hydroxide | Amount to adjust pH to 3.9 |
| Deionized water | Balance |

Example 19

Conditioning Shampoo

| | (wt. %) |
|---|---|
| Sulfate salt 2 (ammonium lauryl ether sulfate with an average of 1.3 moles of EO) | 40.0 |
| Ammonium cumenesulfonate | 0.8 |
| Laurylamidopropyl betaine | 3.0 |
| Polyoxyethylene (16) lauryl ether | 2.0 |
| Stearoxypropyldimethylamine•malate | 0.5 |
| Ethylene glycol distearate | 2.0 |
| Cationic guar gum ("Jaguar C-13S", product of Rhodia) | 0.3 |
| Polypropylene glycol (Mw = 400) | 0.5 |
| Amino-modified silicone derivative ("8500 CONDITIONING AGENT", product of Dow Corning) | 0.8 |
| Sodium chloride | 1.0 |
| Arginine | 0.5 |
| Malic acid | 0.2 |
| Adipic acid | 0.5 |
| Glycolic acid | 0.2 |
| Panthenol | 0.05 |
| Sodium hydroxide | Amount to adjust pH to 5.0 |
| Deionized water | Balance |

Example 20

Conditioning Shampoo

| | (wt. %) |
|---|---|
| Sulfate salt 1 (ammonium lauryl ether sulfate with an average of 1.0 mole of EO) | 16.0 |
| Sodium p-toluenesulfonate | 0.7 |
| Isodecyl glyceryl ether | 1.5 |
| Cocoyl amidopropylbetaine | 1.0 |
| Lauryl hydroxysulfobetaine | 1.0 |
| Lauric acid | 0.5 |
| Oleic acid | 0.7 |
| Distearyl ether | 2.0 |
| Cocoyl benzalkonium chloride | 0.5 |
| Cationic hydroxyethyl cellulose ("Polymer JR-400", product of Amerchol) | 0.4 |
| Ethanol | 0.5 |
| Amino-modified silicone derivative ("8500 CONDITIONING AGENT", product of Dow Corning) | 0.2 |
| Highly polymerized methylpolysiloxane emulsion ("Silicone CF2450", product or Dow Corning Toray) | 2.0 |
| Ceramide II (product of Croda Japan) | 0.05 |
| Fucus vesiculosus extract | 0.05 |
| Malic acid | 0.7 |
| Sodium hydroxide | Amount to adjust pH to 5.0 |
| Deionized water | Balance |

The cleansing compositions obtained in Examples 17 to 20 are each excellent in feeling upon use during shampooing and is effective for straightening the flyaway or waved hair tip which has resulted from the accumulation of damages caused, for example, by hair coloring.

The invention claimed is:

1. A hair cleansing composition comprising the following components (A) to (D):
    (A) from 10 to 20 wt % of a sulfate surfactant represented by the following formula (1):

$$R^1—O—(C_2H_4O)_n—SO_3M \qquad (1)$$

wherein, $R^1$ represents a linear or branched alkyl or alkenyl group having from 10 to 18 carbon atoms, n stands for 0 or a positive integer and M represents sodium or ammonium, wherein the sulfate surfactant is composed of from 30 to 45 wt. % of a sulfate exhibiting n=0, from 18 to 27 wt. % of a sulfate exhibiting n=1, from 10 to 20 wt. % of a sulfate exhibiting n=2 and the balance of sulfates exhibiting n=3 or greater, and contains the sulfates exhibiting n=0 to 2 in a total amount of 70 wt. % or greater based on the total sulfates,
    (B) from 0.2 to 1 wt % of p-toluenesulfonic acid, naphthalenesulfonic acid, or a salt thereof of either acid,
    (C) from 0.3 to 2 wt % of an organic acid selected from the group consisting of malic acid, glycolic acid and lactic acid,
    (D) from 0.5 to 10 wt % of an organic solvent comprising polypropylene glycol having a molecular weight of from 200 to 5000; and optionally, at least one selected from the group consisting of ethanol and benzyl alcohol;
    wherein the composition has a pH at 25° C. of from 3 to 5 when diluted to 20 times the weight with water.

2. The hair cleansing composition according to claim 1, further comprising an amphoteric surfactant.

3. The hair cleansing composition according to claim 1, further comprising an ethylene glycol monofatty acid ester or ethylene glycol difatty acid ester.

4. The hair cleansing composition according to claim 1, wherein the pH at 25° C. is 3.5 to 4.5 when diluted to 20 times the weight with water.

5. A method comprising applying the hair cleansing composition according to claim 1 to the hair of a subject in need thereof of, wherein the hair tip of the hair which has been flyaway or waved owing to damages accumulated by repetition of hair coloring is in need of straightening.

6. The hair cleansing composition according to claim 1, wherein $R^1$ of component (A) is a dodecyl group or a tetradecyl group.

7. The hair cleansing composition according to claim 1 wherein the organic solvent additionally comprises benzyl alcohol.

8. The hair cleansing composition according to claim 1 wherein the organic solvent additionally comprises ethanol and benzyl alcohol.

* * * * *